United States Patent
Ramachandran et al.

(10) Patent No.: US 11,642,031 B2
(45) Date of Patent: May 9, 2023

(54) MEDICAL DEVICE INSERTION AND EXIT INFORMATION USING DISTRIBUTED FIBER OPTIC TEMPERATURE SENSING

(71) Applicant: KONINKLIJKE PHILIPS N.V., Eindhoven (NL)

(72) Inventors: Bharat Ramachandran, Morganville, NJ (US); Robert Manzke, Bönebüttel (DE); Raymond Chan, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1135 days.

(21) Appl. No.: 16/175,887

(22) Filed: Oct. 31, 2018

(65) Prior Publication Data

US 2019/0059743 A1  Feb. 28, 2019

Related U.S. Application Data

(62) Division of application No. 14/240,032, filed as application No. PCT/IB2012/054379 on Aug. 27, 2012, now abandoned.

(60) Provisional application No. 61/530,443, filed on Sep. 2, 2011.

(51) Int. Cl.
| | |
|---|---|
| *A61B 5/01* | (2006.01) |
| *G01K 3/14* | (2006.01) |
| *G01K 11/3206* | (2021.01) |
| *G01L 1/24* | (2006.01) |
| *A61B 5/00* | (2006.01) |

(Continued)

(52) U.S. Cl.
CPC .......... *A61B 5/015* (2013.01); *A61B 5/0084* (2013.01); *A61B 5/061* (2013.01); *G01K 3/14* (2013.01); *G01K 11/3206* (2013.01); *G01L 1/246* (2013.01); *A61B 34/20* (2016.02)

(58) Field of Classification Search
None
See application file for complete search history.

(56) References Cited

U.S. PATENT DOCUMENTS

| | | |
|---|---|---|
| 5,653,539 A | 8/1997 | Rosengaus |
| 5,730,134 A | 3/1998 | Dumoulin et al. |
| 7,976,537 B2 | 7/2011 | Lieber et al. |

(Continued)

FOREIGN PATENT DOCUMENTS

| | | |
|---|---|---|
| CN | 101099657 A | 1/2008 |
| DE | 102008014745 A1 | 10/2009 |

(Continued)

OTHER PUBLICATIONS

Kreger, S.T. et al. "High resolution distributed strain or temperature measurements in single and multi mode fiber using swept wavelength interferometry". Institute of Electronics, Informayion and Communication Engineers, Optical Fiber Sensors, Conference Paper, Mexico, (2006).

*Primary Examiner* — Patricia J Park

(57) ABSTRACT

A system, device and method include a sensing enabled device having an optical fiber configured to perform distributed sensing of temperature-induced strain. An interpretation module is configured to receive optical signals from the optical fiber within a body and interpret the optical signals to determine one or more temperature transition points sensed by the sensing enabled device for image registration.

5 Claims, 4 Drawing Sheets

(51) Int. Cl.
*A61B 5/06* (2006.01)
*A61B 34/20* (2016.01)

(56) References Cited

U.S. PATENT DOCUMENTS

| | | |
|---|---|---|
| 8,009,946 B2 | 8/2011 | Xia et al. |
| 8,298,227 B2 | 10/2012 | Leo et al. |
| 8,678,642 B2 | 3/2014 | Jester et al. |
| 8,773,650 B2 | 7/2014 | Froggatt et al. |
| 9,155,476 B2 | 10/2015 | Fojtik |
| 2003/0060762 A1* | 3/2003 | Zvuloni ............... F25B 9/02 604/113 |
| 2005/0150739 A1 | 7/2005 | Rosello |
| 2006/0241484 A1* | 10/2006 | Horiike ............ A61B 8/4416 600/467 |
| 2007/0156019 A1 | 7/2007 | Larkin et al. |
| 2007/0156212 A1* | 7/2007 | Saxena ............... A61B 18/18 607/102 |
| 2011/0015528 A1* | 1/2011 | Kobayashi ....... G02B 23/2469 600/477 |
| 2011/0087112 A1 | 4/2011 | Leo et al. |
| 2011/0116743 A1 | 5/2011 | Arkwright et al. |
| 2011/0172519 A1 | 7/2011 | Cao et al. |
| 2011/0319910 A1* | 12/2011 | Roelle .................. A61B 34/30 606/130 |
| 2012/0197097 A1 | 8/2012 | Chan et al. |
| 2015/0094570 A1 | 4/2015 | Fojtik |

FOREIGN PATENT DOCUMENTS

| | | |
|---|---|---|
| JP | 2008173397 A | 7/2008 |
| RU | 87081 U1 | 9/2009 |

\* cited by examiner

MEDICAL DEVICE INSERTION AND EXIT INFORMATION USING DISTRIBUTED FIBER OPTIC TEMPERATURE SENSING

CROSS-REFERENCE TO PRIOR APPLICATIONS

This application is a divisional of prior application Ser. No. 14/240,032 filed Feb. 21, 2014. Ser. No. 14/240,032 is a U.S. National Phase application under 35 U.S.C. § 371 of International Application serial no. PCT/IB2012/054379, filed on Aug. 27, 2012, which claims the benefit of U.S. Application Ser. No. 61/530,443, filed on Sep. 2, 2011. These applications are hereby incorporated by reference herein.

This disclosure relates to medical instruments and more particularly to shape sensing optical fibers in medical applications for evaluating and determining insertion/exit or other information for medical devices.

Minimally invasive procedures involve making small incisions or keyholes, for inserting devices to perform a procedure. In many instances, it is important to know the point of insertion relative to the device and patient, for example, to determine the portion of the device currently residing within the body versus outside the body. The devices inserted are typically elongated and may extend a significant distance into the body. In addition, the length may change dynamically during a procedure changing how much of the instrument is inside the body.

In accordance with the present principles, a system, device and method include a sensing enabled device having an optical fiber configured to perform distributed sensing of temperature-induced strain. An interpretation module is configured to receive optical signals from the optical fiber within a body and interpret the optical signals to determine one or more temperatures or temperature gradients of the device.

A workstation includes a medical instrument including a sensing device having at least one optical fiber and configured to perform distributed sensing of temperature-induced strain. A processor is provided, and memory is coupled to the processor having an interpretation module stored therein and configured to receive optical signals from the at least one optical fiber within a subject and interpret the optical signals to determine at least one temperature or temperature gradient of the device. A display is coupled to the processor and configured to display temperature and/or temperature gradient information relative to the subject.

A method includes collecting strain data from a fiber optic strain sensing device disposed within at least two different temperature regions; determining a temperature transition point between the at least two different temperature regions based on the strain data and locating the transition point relative to a medical device to find a specific reference location.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

Figure 1:
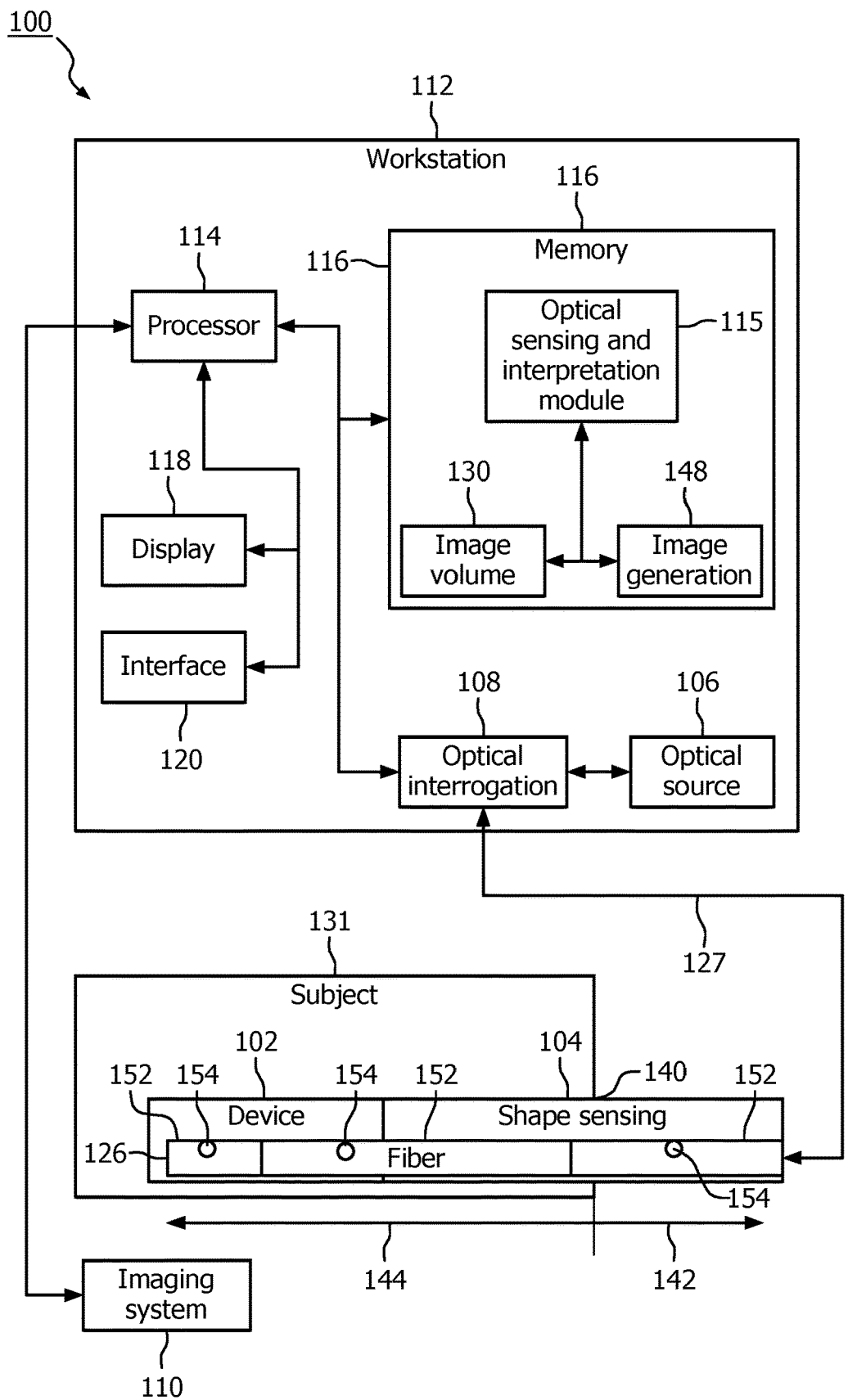
FIG. 1 is a block/flow diagram showing a system and workstation which employ a temperature/shape sensing system in accordance with one embodiment.

In accordance with the present principles, a system for determining an insertion/exit position of a medical instrument and for determining how much of an instrument is internal to a patient versus external to the patient is provided. In accordance with one particularly useful embodiment, a fiber optic strain sensing device is employed with a medical instrument. Shape sensing based on fiber optics exploits the inherent backscatter in a conventional optical fiber. A principle involved makes use of distributed strain measurement in the optical fiber using characteristic Rayleigh backscatter patterns or other reflective features. A fiber optic strain sensing device is mounted on or integrated in a medical instrument such that the fiber optic sensing device can show a shape as well as a spatially resolved temperature distribution for the medical instrument. In one embodiment, temperature is employed to measure the position of entry/exit of the fiber enabled device within the body. This information can be employed to calculate a length of the instrument within the body as the device is inserted and manipulated further within the body in a real-time fashion.

In one example, four or more core fibers may be employed where one core is located in the center of the cross-section, in such an arrangement one is able to separate strain due to bending from temperature effects (e.g., when axial strain (tension) is not present, or if the tension is known and controllable (or can be calibrated out)). Combined shape and temperature sensing may be provided in one embodiment. In other embodiments, only temperature effects may be measured with as few as one optical fiber.

In one illustrative embodiment, a system performs distributed fiber optic sensing of strain and temperature and is capable of reconstructing the shape of an elongated medical device, where a spatially resolved temperature measurement is used to identify temperature gradients caused by transitions between locations inside and outside the body. The strain measurements may be employed to determine the device shape and determine specific locations along the device using temperature gradients. The system is able to determine the portion of the device residing within domains of different temperatures, e.g., inside versus outside the human body, inside versus outside a thermally treated zone (e.g., an ablation zone), etc.

Furthermore, detection of a fixed insertion point can be used to specify a patient specific reference launch region that moves in a patient's coordinate frame of reference rather than a lab frame of reference. For accurate shape sensing, ambient temperature around the shape sensing device is employed to calibrate the device for intra-procedural use, e.g., a shape sensing component operating at room temperature outside the body and a second component in-vivo that operates at body temperature. Shape sensing accuracy in both segments is necessary and therefore, segment specific temperature calibration is preferred.

It should be understood that the present invention will be described in terms of medical instruments; however, the teachings of the present invention are much broader and are applicable to any fiber optic instruments. In some embodiments, the present principles are employed in tracking or analyzing complex biological or mechanical systems (e.g., plumbing systems or the like). In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Referring now to the drawings in which like numerals represent the same or similar elements and initially to FIG. 1, a system 100 for performing a procedure using temperature sensing enabled devices is illustratively shown in accordance with one embodiment. System 100 may be employed with and is applicable for all applications for interventional and surgical procedures that employ fiber optic shape sensing. Distributed fiber optic sensing of strain and temperature may be employed to reconstruct the shape and/or temperature of an elongated medical device 102. Spatially resolved temperature measurement is used to identify temperature gradients caused by transitions between locations inside and/or outside a body 131. The strain measurements are employed to determine device shape and determine specific locations along the device having temperature gradients. Portions of the device 102 residing within domains of different temperatures, e.g., inside versus outside the human body or inside versus outside a thermally treated zone, may be determined.

System 100 may include a workstation or console 112 from which a procedure is supervised and/or managed. Workstation 112 preferably includes one or more processors 114 and memory 116 for storing programs and applications. Memory 116 may store an optical sensing and interpretation module 115 configured to interpret optical feedback signals from a shape and/or temperature sensing device or system 104. Optical sensing module 115 may be configured to use the optical signal feedback (and any other feedback, e.g., electromagnetic (EM) tracking, live multimodality imaging data, or other monitoring data available within the clinical environment) to reconstruct deformations, deflections and other changes associated with a medical device or instrument 102 and/or its surrounding region. The medical device 102 may include a catheter, a guidewire, a probe, an endoscope, a robot, an electrode, a filter device, a balloon device, or other medical component, etc. In a particularly useful embodiment, sensing device 104 includes a temperature sensing configuration which may be employed with or independently from the medical device 102.

A temperature sensing system includes module 115 and shape/temperature sensing device 104 mounted on or integrated into the device 102. The sensing system includes an optical interrogator 108 that provides selected signals and receives optical responses. An optical source 106 may be provided as part of the interrogator 108 or as a separate unit for providing light signals to the sensing device 104. Sensing device 104 includes one or more optical fibers 126 which are coupled to the device 102 in a set pattern or patterns. The optical fibers 126 connect to the workstation 112 through cabling 127. The cabling 127 may include fiber optics, electrical connections, other instrumentation, etc., as needed.

Sensing device 104 with fiber optics may be based on fiber optic Bragg grating sensors. A fiber optic Bragg grating (FBG) is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

A fundamental principle behind the operation of a fiber Bragg grating is Fresnel reflection at each of the interfaces where the refractive index is changing. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optical sensors. In an FBG sensor, the measurand (e.g., temperature or strain) causes a shift in the Bragg wavelength.

One advantage of this technique is that various sensor elements can be distributed over the length of a fiber.

Incorporating three or more cores with various sensors (gauges) along the length of a fiber that is embedded in a structure permits a three dimensional form of such a structure to be precisely determined, typically with better than 1 mm accuracy. Along the length of the fiber, at various positions, a multitude of FBG sensors can be located (e.g., three or more fiber sensing cores). From the strain measurement of each FBG, the temperature and the curvature of the structure can be inferred at that position. From the multitude of measured positions, the total three-dimensional form is determined and temperature differences can be determined.

As an alternative to fiber-optic Bragg gratings, the inherent backscatter in conventional optical fiber can be exploited. One such approach is to use Rayleigh scatter in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in three or more cores running within a single length of multi-core fiber, the 3D shape, temperature and dynamics of the surface of interest can be followed.

An imaging system 110 may be employed for in-situ imaging of a subject 131 during a procedure. The imaging system 110 may be incorporated with the device 102 (e.g., intravenous ultrasound (IVUS), etc.) or may be employed externally to the subject 131. Imaging system 110 may also be employed for collecting and processing pre-operative images (e.g., image volume 130) to map out a region of interest in the subject to create an image volume for registration and with shape/temperature sensing space.

Figure 2:
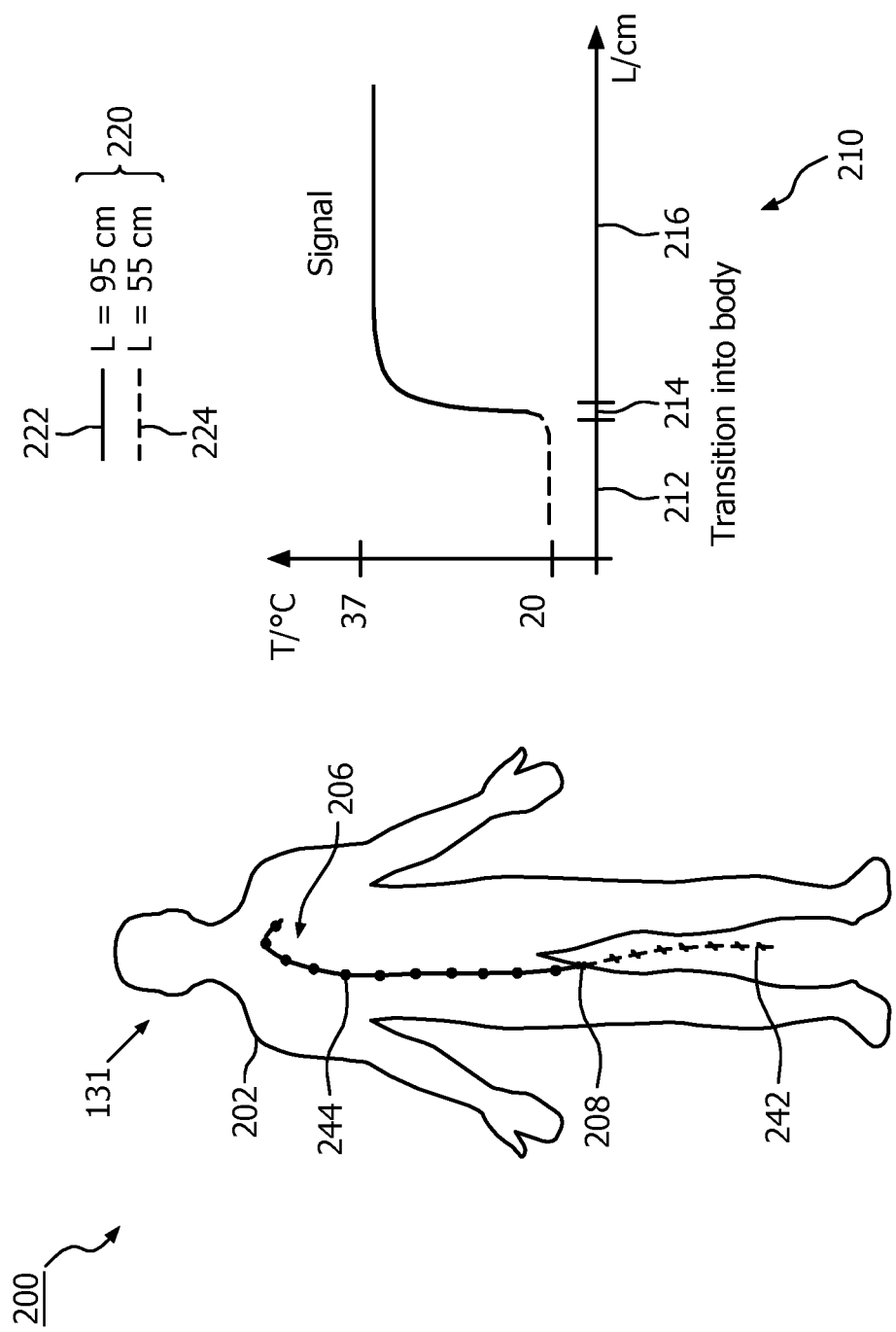
FIG. 2 is a graphic image showing a possible display for indicating a reference position between two temperature regions in accordance with the present principles.

In one embodiment, workstation 112 includes an image generation module 148 configured to receive at least one temperature gradient of the device 102 and register an image to the at least one temperature gradient or otherwise display the results from the sensing device 104. Workstation 112 includes a display 118 for viewing internal images of a subject (patient) 131 and may include an overlay or other image showing an entry/exit point of the device 102 (and/or sensing device 104). FIG. 2 shows an illustrative display image. Imaging system 110 may include a fluoroscopy system, a computed tomography (CT) system, an ultrasonic system, etc. Display 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

In another embodiment, system 100 includes a method to compute a point of entry 140 of the shape/temperature sensing enabled device 102 within the body 131 without employing any other imaging or tracking scheme or relying on any outside technology or user observation/intervention. The system 100 computes the point of entry 140 dynamically in real-time and to know the exact portion of the sensing device 104 entering the body 131. For a fiber-optic shape sensing system, detection of the fixed insertion point 140 can be employed to specify a patient specific reference launch region that moves in the patient's coordinate frame of reference rather than a frame of reference of the environment (e.g., the lab or operating room). For accurate shape/temperature sensing performance, the ambient temperature around the optical fiber 126 is needed as a factor to calibrate the device 104 for intra-procedural use. For example, the ambient room temperature dominates a first portion 142 of the sensing device 104 outside the body, and a second portion 144 in vivo operates at body temperature. Shape sensing accuracy in both segments is needed and therefore, segment specific temperature calibration is preferred.

In one embodiment, each of N segments 152 of optical fiber 126 may include a temperature reference component 154 to provide a calibration temperature for each respective segment 152. This may be employed during a procedure or as a calibration step in advance or after the procedure. The optical measurements recorded by the distributed fiber sensor 104 can be calibrated into accurate temperature values by use of the known fiber shapes and tension, in combination with the independent temperature reference 154, e.g., a thermistor reading, or from exposure of the fiber to known temperatures and temperature changes in a calibration step.

Referring to FIG. 2, a graphic or image 200 showing a possible display (e.g., on display 118) is illustratively depicted. A rendering 202 of a patient may include a generic outline or may include an actual real-time or pre-recorded image of the patient or portion of the patient. The image 200 may include a rendering 206 of the sensing device 104 and may show different textures or colors relative to an entry point 208 (temperature change). For example, a first portion 242 of the sensing device 104 is outside the body 131, and a second portion 244 is inside the body 131.

The graphic 200 includes a graph 210 that provides a real-time means of calculating the length of the shape sensing enabled device 102 that is within the body 131, which may be needed for, e.g., endoluminal applications both diagnostic and therapeutic to perform a biopsy from a desired target lesion, rather than from the wrong region due to overshoot/undershoot of device insertion. In so doing, improvements in diagnostic yield may be realized during interventional procedures. The graph 210 shows an external temperature region 212 and an internal temperature region 216 and a transition temperature region 214. The transition temperature region 214 provides a transition into the body 131, which is employed to determine the entry point 208. In addition, a running computation 220 may be displayed showing an inserted length 222 and an external length 224. Other graphics and visual tools are also contemplated and may be employed.

The temperature of the human body at 37 degrees C. is higher than the ambient temperature in an operating room or an interventional suite (around 20 degrees C., e.g., with air conditioning, etc.). As a result, at the point when the fiber device enters into the body, the fiber will undergo a gradient or gradual change in temperature from 20 to 37 degrees C. (assuming normal human body temperature). This position can be dynamically detected during advancement of the device 104. Thermal capacities introduced by the material surrounding the fiber, however, may lead to larger time constants affecting the response time of the system to temperature changes. These may be accounted for in the design or in the computation, for example.

In an alternate embodiment, shape/temperature sensing data may be matched to imaging data, both pre-operative and intra-operative, as long as the point of entry 208 is visible in the imaging space. For example, an image of the body 131 and a rendering of the sensing device 104 may be displayed together. The entry point 208 may provide a common reference to register both spaces. This addresses the problems faced in registration when either the fiber 126 itself is not visible in the field of view, or if the fiber segment 152 that is present lacks sufficient structural detail to allow for unambiguous fusion (e.g., the fiber device appears as a single line extending through the field of view).

Figure 3:
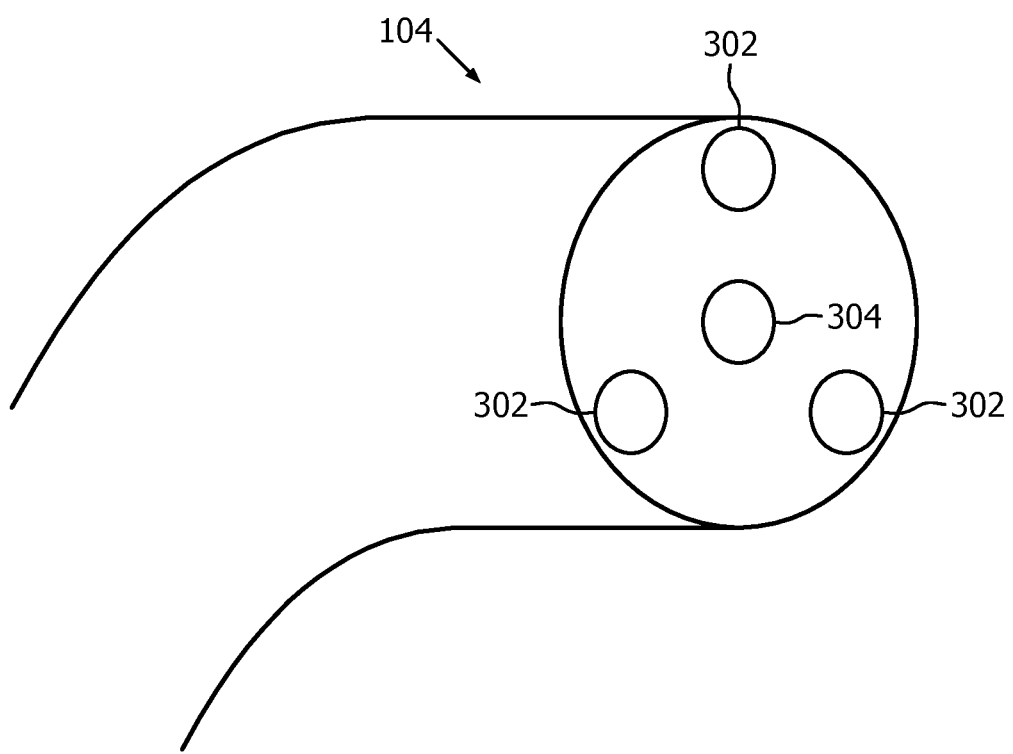
FIG. 3 is a diagram of a sensing device with a cross-section depicted showing multiple optical fibers in accordance with one illustrative embodiment.

Referring to FIG. 3, a shape/temperature sensing device 104 is illustratively shown with a cross-sectional view. An optical fiber may be employed to measure strain and is also sensitive to temperature. In one embodiment, three outer fiber cores 302 are disposed about a fourth central core 304. With this combination, separate measurements of strain may be obtained leading to shape (cores 302) and spatially resolved temperature (along the length) (core 304). The configuration works best if there is no axial strain present. In most scenarios, axial strain of the device 104 is negligible since the device is not stretched along its length, and therefore it is reasonable to assume that the primary influence in the central core 304 is due to temperature. Other configurations may also be employed to zero out or account for axial strain if present. For example, a second central core (not shown) with different properties from the first core may be provided such that physical strain and temperature strain may be distinguished. The second central core may be provided with different properties or different doping material to give a different refractive index and/or coefficient of expansion. These same features or differences can also be applied to the outer cores (not just central the central core or cores) where each core could have a different property such that measurement differences would permit multiple solutions to resolve axial strain, temperature values, etc.

Changes in temperature along the length of the device 104 are monitored to dynamically determine the insertion point (208) or more generally determine positions within different temperature domains. As mentioned, this can be combined with pre-operative imaging to predict whether a target is being approached. It can also be used to match and register the pre-operative imaging to the shape sensing system when the point of entry is also visible in the imaging modality.

With the configuration of four cores (302, 304), strains from temperature can be easily distinguished from geometrical strains. The strains in cores 302 may be employed to resolve temperature regions along the fibers as the geometry indicated by the cores 302 will provide positional information relative to the information collected from the central core 304. In addition, the fiber optic sensor 104 may provide additional optical measurements, such as backscatter, etc., which can be used to more accurately solve ill-posed estimation problems by teasing apart temperature from deformation-induced changes in the optical backscatter.

It should be understood however that a single fiber core may be employed as a temperature sensor. This is particularly useful where other strains in the single fiber are known. In fiber configurations with even more cores (e.g., say, up to 7 cores), the cores are preferably evenly or symmetrically distributed about the central core. In one example, seven cores may be employed with 6 exterior cores in a hexagonal form and one core in the center. Other configurations are also contemplated.

A physical length and index of refraction of a fiber are intrinsically sensitive to environmental parameters of temperature and strain and, to a much lesser extent, pressure, humidity, electromagnetic fields, chemical exposure etc. The wavelength shift, $\Delta\lambda$ or frequency shift, $\Delta\nu$ of the backscatter pattern due to a temperature change, $\Delta T$, or strain along the fiber axis, $\varepsilon$, is: $\Delta\lambda/\lambda=-\Delta\nu/\nu=K_T\Delta T+K_\varepsilon$ where $$K_\varepsilon = 1 - \frac{n_{eff}^2}{2}(p_{12} - \mu(p_{11} + p_{12})).$$

The temperature coefficient $K_T$ is a sum of the thermal expansion coefficient $\alpha$ and the thermo-optic coefficient $\xi=1/n(\partial n/\partial T)$, with typical values of $0.55\times10^{-6}$ C.$^{-1}$ and $6.1\times10^{-6}$ C.$^{-1}$, respectively for germanium-doped silica core fibers. The strain coefficient $K_\varepsilon$ is a function of group index n (or $n_{eff}$); the components of the strain-optic tensor, $p_{ij}$ and Poisson's ratio, $\mu$. Usual values given for n, $p_{12}$, $p_{11}$ and $\mu$ for germanium-doped silica yield a value for Kε of about 0.787. Thus, a shift in temperature or strain may be a linear scaling (for moderate temperature and strain ranges) of the spectral frequency shift $\Delta\nu$. This linear model does not apply if strains approach the elastic limit of the fiber, or temperatures approach the glass transition temperature of the fiber.

The use of temperature changes detected along the fiber length permits piecewise constant temperature calibration and segment specific shape reconstruction to be applied to each domain of the fiber sensor (104). This ensures shape tracking accuracy in each region despite the presence of a temperature gradient at the insertion point (which might normally degrade the performance of shape sensing/localization).

Other applications of the present principles may include pulmonology or other endoluminal and endovascular applications where a position of a target, such as a lesion is known in pre-operative computed tomography (CT) images. Knowing this, the path that a pulmonologist has to traverse to reach the target and the length of the path are also known. In accordance with the present principles, the clinician also knows the length of the device that has been moved within the body, and this coupled with 3D shape information from the device would be significant in improving the yield of the procedure. The examples described should not be construed as limiting. Other endoluminal procedures that could benefit from the present principles include applications in gastroenterology, colorectal procedures, gynecology, urology, etc. The sensing device 104 may be incorporated in one or more of the following devices: cystoscopes, ureteroscopes, rhinolaryngoscopes, gastroscopes, colonoscopes, esophagoscopes, etc.

Figure 4:
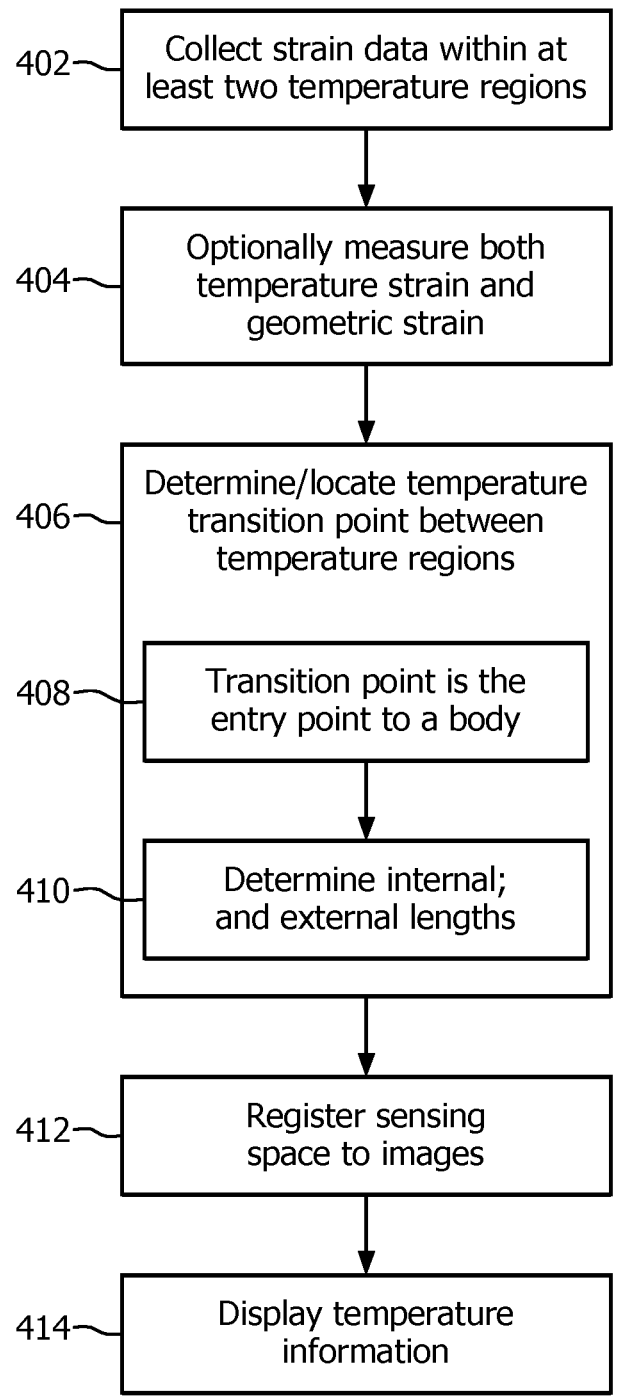
FIG. 4 is a block/flow diagram showing a system/method for gathering and employing sensed strain data for determining temperature transitions as reference positions in accordance with another illustrative embodiment.

Referring to FIG. 4, a method for determining a temperature transition point for deciphering a reference location is illustratively shown in accordance with one embodiment. In block 402, strain data is collected from a fiber optic strain sensing device disposed within at least two different temperature regions. The sensing device may include a first portion having a first temperature and a second portion having a second temperature, and the first portion is internal to a body, and the second portion is external to the body. In this instance, the transition point includes a point of entry in the body. In another example, the first portion may include a temperature treated zone (ablation zone, cryogenic treated zone, etc.), and the second portion includes a reference temperature zone. The transition point(s) may be employed to determine an entry/exit point to the body, determine a distance in the body to a target, determine an ablation region, etc.

The strain data may include geometrical data for determining a shape of a medical device as well as temperature transitions. In block 404, the sensing data may include temperature induced strain and geometrically induced strain. The sensing device may include at least four optical fibers configured with three optical fibers surrounding a central optical fiber such that the three optical fibers measure geometric strain and the central optical fiber measures a temperature induced strain. Other configurations are also contemplated.

In block 406, a temperature transition point is determined between the at least two different temperature regions based on the strain data. Any number of regions may be employed. In block 408, the transition point is located relative to a body and/or a medical device to find a specific reference location. In block 410, locating the transition point may include determining a length of the first portion and a length of the second portion.

In block 412, an image of the body may be registered to temperature/shape sensing space using the temperature transition point as a reference. In block 414, temperature information is displayed. The transition point and/or the temperature gradient may be displayed for a clinician to improve accuracy, yield, etc. of a procedure.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for medical device insertion and exit information using distributed fiber optic temperature sensing (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system, comprising:

a sensing enabled device having at least one optical fiber configured to perform distributed sensing of temperature-induced strain; and an interpretation module configured to receive optical signals from the at least one optical fiber comprising strain data from within a body and interpret the optical signals to determine a temperature transition point between at least two different temperature regions based on the strain data;

the system being configured to register the sensing enabled device to an image of the body using the temperature transition point as a reference; and wherein the temperature transition point is the only reference used to register the sensing enabled device to the image of the body.

2. The system of claim 1, wherein the at least one optical fiber of the sensing enabled device includes a first portion having a first temperature and a second portion having a second temperature, and wherein the interpretation module determines the temperature transition point by using a length of the first portion and a length of the second portion.

3. The system of claim 1, wherein the sensing enabled device includes a first portion having a first temperature and a second portion having a second temperature, and wherein the first portion includes a temperature treated zone and the second portion includes a reference temperature zone.

4. The system of claim 1 wherein strain data is collected from three or more temperature regions.

5. The system of claim 1, wherein the at least two different temperature regions are internal to the body.

* * * * *